United States Patent [19]

Daily

[11] Patent Number: 4,665,927
[45] Date of Patent: May 19, 1987

[54] INTRAOPERATIVE TEMPERATURE PROBE

[75] Inventor: Pat O. Daily, Rancho Santa Fe, Calif.

[73] Assignee: Pat O. Daily, San Diego, Calif.

[21] Appl. No.: 757,169

[22] Filed: Jul. 22, 1985

[51] Int. Cl.$^4$ .................................................. A61B 5/00
[52] U.S. Cl. ........................................ 128/736; 374/110
[58] Field of Search ............. 128/736, 656, 664, 670; 374/110

[56] References Cited

U.S. PATENT DOCUMENTS

| | | | |
|---|---|---|---|
| 2,012,112 | 5/1932 | States | 128/736 |
| 2,025,534 | 12/1935 | Sheard et al. | 219/19 |
| 2,816,997 | 2/1955 | Conrad | 128/736 |
| 3,313,293 | 4/1967 | Chesebrough et al. | 128/2.1 |
| 3,951,136 | 4/1976 | Wall | 128/2.06 |
| 4,176,660 | 12/1979 | Mylrea et al. | 128/736 |
| 4,182,313 | 1/1980 | Aslan | 128/736 |
| 4,253,469 | 3/1981 | Aslan | 128/736 |
| 4,369,795 | 1/1983 | Bicher et al. | 128/736 |
| 4,378,023 | 3/1983 | Trabucco | 128/785 |
| 4,397,314 | 8/1983 | Vaguine | 128/804 |
| 4,402,323 | 9/1983 | White | 128/642 |
| 4,408,610 | 10/1983 | Sarnoff | 128/642 |
| 4,410,756 | 10/1983 | Schwagerman | 374/110 |
| 4,411,266 | 10/1983 | Cosman | 128/303.18 |
| 4,444,195 | 4/1984 | Gold | 128/642 |
| 4,445,778 | 5/1984 | Twersky et al. | 374/110 |
| 4,476,872 | 10/1984 | Perlin | 128/642 |
| 4,481,953 | 11/1984 | Gold et al. | 128/786 |

FOREIGN PATENT DOCUMENTS 2070934 10/1981 United Kingdom ............... 128/736

Primary Examiner—Kyle L. Howell
Assistant Examiner—Randy Citrin
Attorney, Agent, or Firm—Baker, Maxham & Jester

[57] ABSTRACT

A temperature probe for insertion into the tissue of an organ, such as a heart, during surgery comprises an elongated needle made of plastic with a large button type head, and having one or more sensing elements disposed at selected positions along the length thereof for sensing the temperatures at various depths, with a surface temperature sensor positioned just beneath the head in the needle.

14 Claims, 5 Drawing Figures

INTRAOPERATIVE TEMPERATURE PROBE

BACKGROUND OF THE INVENTION

The present invention relates to temperature sensing devices and pertains particularly to an improved temperature probe for insertion into animal tissue.

During surgery on organs such as the heart, it is desirable to know the temperatures of the organ during this operation. Temperature sensors which are currently available are in the form of a stainless steel needle for insertion into the organ for sensing the internal temperature of the organ.

These presently available temperature sensors have a number of drawbacks. For example, due to the high thermal conductivity of stainless steel, heat is conducted very rapidly along the needle. The resultant temperature tends to indicate an average temperature over the length of the needle. This is undesirable in most instances in that it does not provide means for obtaining a reasonably accurate point location temperature nor an accurate temperature gradient measurement between spaced positions.

Another drawback to the stainless steel needle temperature sensor is the rigidity thereof. The stainless steel needle is reasonably rigid or stiff and when inserted into the organ tends to go through the muscle fibers rather than around them. This increases potential injury and trauma of such use.

The lack of flexibility of such needles also has a tendency to cause further injury if accidentally knocked out to the tissue. This is particularly so where side forces are placed on the needle. In such instances, the needle tends to rip the tissue.

The applicant has discovered that the needles can be made of certain plastics and thereby have certain advantages over stainless steel needles. Plastics according to the invention have lower thermal conductivity and thereby improved accuracy. The use of plastic also allows a certain flexibility in the needle that reduces tissue stress during probe use.

It is therefore desirable that a flexible stable probe for insertion into animal tissue for accurately sensing the temperature thereof at one or multiple positions during surgery be available.

SUMMARY AND OBJECTS OF THE INVENTION

It is the primary object of the present invention to provide an improved temperature sensing probe.

In accordance with the primary aspect of the present invention, a temperature sensing probe comprises an elongated non-metallic needle having flexibility and one or more sensing elements along the length of the probe for sensing temperature at selected positions, such as internally, at the surface and intermediate thereof of an animal organ.

BRIEF DESCRIPTION OF THE DRAWINGS

The above and other objects and advantages of the present invention will become apparent from the following description when read in conjunction with the drawings wherein.

DETAILED DESCRIPTION OF A PREFERRED EMBODIMENT

Figure 1:
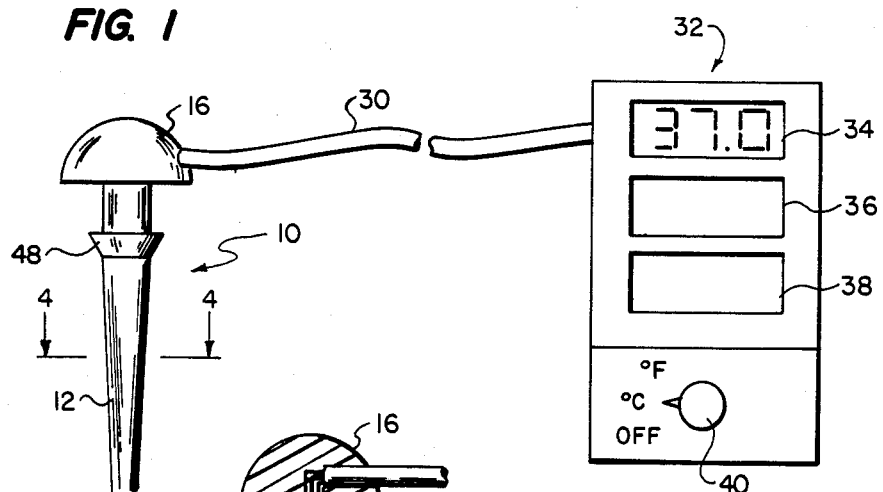
FIG. 1 is an elevation view of a probe in accordance with a preferred embodiment of the invention shown in combination with a temperature monitoring unit.

Referring to FIG. 1 of the drawings, a temperature probe in accordance with the present invention is illustrated and designated generally by the numeral 10. This probe is constructed of a flexible plastic and comprises an elongated needle member 12 having a distal end 14 defined by a penetrating point for insertion into the tissue of an animal organ. The penetrating end or point 14 preferably has a generally wedge shape, such as formed by a bevel cut across the end thereof. This provides a tip that along with the flexibility of the needle shank can slip between muscle fibers rather than cut through them. The needle also includes a rounded or somewhat semi-spherical button shaped head 16 on the proximal end of the needle. This head facilitates the insertion of the probe into the tissue and the removal thereof.

Figure 2:
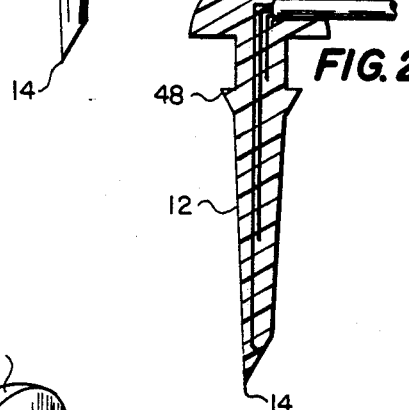
FIG. 2 is a sectional view showing details of construction of the probe of FIG. 1.

The probe as illustrated in FIG. 2 is preferably provided with one or more sensing elements 18, 20 and 22 which are disposed at selected positions along the length of the needle. These are positioned with sensor 18 at the tip for determining or sensing the temperature at a selected depth internally of the organ. Sensor 22 senses and determines the surface temperature, and sensor 20 determines an intermediate temperature. One, and as many as three sensing elements can be disposed along the needle to sense the respective temperatures. Materials often used in thermocouples are iron, constantan, copper, chromel, alumel, and others.

In a preferred form, the sensors may be either thermisters or thermocouples. The illustrated sensors are thermocouples which are connected by suitable pairs of conductors 24, 26 and 28 respectively which form the respective beads and connect through an insulated wire or the like 30 to a visual monitoring unit 32.

Preferably, the visual monitoring unit would have means for instantaneously monitoring all three or more of the temperatures by means of digital displays 34, 36 and 38. In addition, the monitor would also include selector control means 40 for changing the temperature scale to either Fahrenheit or Centigrade. Monitoring units of this type with multiple display are capable of being constructed by those of skill using existing technology. It is understood however that the illustrated combination, including multiple sensing elements and multiple displays, are not believed to be known in the art.

The needle is constructed of a flexible plastic rather than the typical stainless steel of the prior art probes. It has been found that a number of suitable plastic materials such as polycarbonate, acrylonitrile-butadiene-styrene (ABS), Nylon, acetyl, and polyvinylchloride (PVC) may be utilized. These plastics have advantages over stainless steel because of their lower thermal conduction rate which provides a more precise temperature reading for a selected point. This construction thus enables a more accurate separation of the temperature gradients between the various sensing elements along the shank of the needle. It also provides for a more accurate point reading of temperature.

The plastic needle also has the advantage of being relatively flexible. The needle should be stiff enough to enable insertion into the organ, yet flexible enough that it will yield to the muscle fiber and pass around it rather than through it. This will also enable it to yield and slide out rather than ripping the tissue if side pressure is placed on it.

The needle may be made in several lengths for different applications. The needle was developed initially for use in heart surgery and would be available in various sizes for this and other uses. Ideally, three size probes for three different areas of the heart, the septum, the left ventrical and the right ventrical would be used.

The needle for the septum is on the order of about three centimeters in length or just slightly over one inch with an outside diameter of about forty-three thousandths of an inch. The head of the needle has a preferred diameter of about one-quarter of an inch with a thickness of about one-tenth of an inch. The sizes may vary, but the indicated dimensions are preferred for the specified application.

As previously mentioned, the probe can be made out of any suitable plastic material, and constructed in several ways. Currently, polycarbonate injection molding is preferred. This approach is by the molding of the entire probe as a unit complete with the temperature sensing elements 18, 20, and 22 and their leads 24, 26, and 28 in place as shown in FIG. 2. The needle can be molded with one or more of the sensing elements therein.

Figure 3:
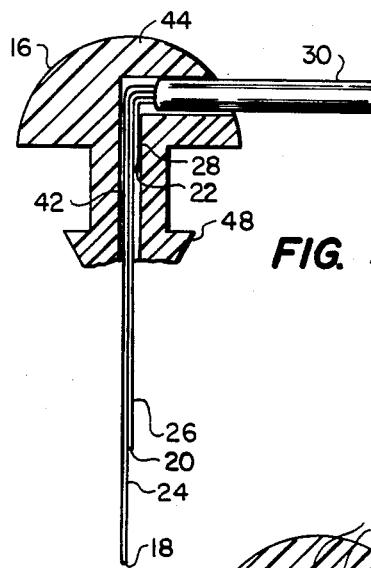
FIG. 3 is an enlarged partial view in section showing details of the head of an alternate construction the probe.

An alternate approach is injection molding the probe with a central bore 42 extending through the top and along the needle as shown in FIG. 3. A slot opening 44 is formed in the top of the probe to accommodate the positioning of the leads as shown. The temperature sensing elements and the leads are inserted into the bore at the top and when properly positioned the leads are positioned to extend out the side of the head as shown. The bore 42 and slot 44 filled with an epoxy 50 for anchoring the leads and sensors in place. The internal bore would have a diameter of on the order of about nineteen thousandths (0.019) of an inch. This approach avoids possible molding problems, but increases the labor required for production.

Figure 5:
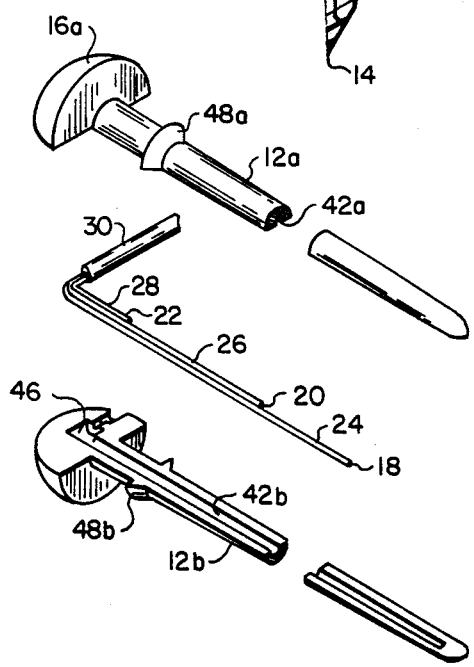
FIG. 5 is an exploded view of another mode of construction of the probe.
Figure 4:
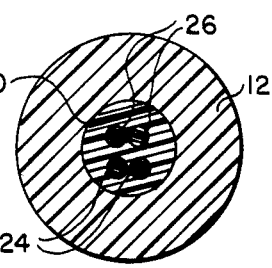
FIG. 4 is a section view taken across the needle of FIG. 2.

An additional approach is to mold the probe in two halves as shown in FIG. 5 with subsequent assembling of the halves. As illustrated in FIG. 5, the barrel is constructed of two complementary halves 12a and 12b such that they may be assembled post injection molding.

The two halves of the probe both include a central elongated half-bore 42a and 42b extending the length of the probe with a closed end at the point or distal end. The bore halves 42a and 42b intersects and communicates with a multiple step bore 46 in the cap or head of the probe. The bore 46 has a reduced diameter portion intermediate the ends of the bore for gripping end of the cable 30 as shown in FIG. 3. The cannula or bore halves 42a and 42b receives the thermocouple beads and sensing elements thereof and are bonded in place with an epoxy or the like. This approach has the disadvantage of added labor cost.

Other approaches to formation of the needle are also possible.

While I have illustrated and described my invention by means of specific embodiments, it is to be understood that numerous changes and modifications may be made therein without departing from the spirit and scope of the invention as defined in the appending claims.

I claim:

1. A temperature probe for insertion into animal tissue, comprising:
    an elongated needle including a solid body formed of a plastic having a low coefficient of thermal conductivity, said needle having a distal end having tip means for penetrating animal tissue and a proximal end defined by an enlarged cap;
    a plurality of temperature sensing elements embedded within said needle body, said plurality of temperature sensing elements being disposed in longitudinally spaced relationship between said needle distal end and said proximal end with said sensing elements thermally isolated from each other by said plastic, one of said plurality of temperature sensing elements being positioned adjacent said tip and another of said plurality of temperature sensing elements being positioned adjacent said cap; and
    a plurality of conductive leads each connected respectively to one of said sensing elements disposed within said needle body and exiting said needle body at the proximal end thereof for connection to associated indicating means.

2. A temperature probe according to claim 1 wherein said needle is constructed of a plastic taken from the group consisting of polycarbonate, ABS, PVC, Nylon, and aceytl.

3. A temperature probe according to claim 1 wherein said sensing elements are thermocouples.

4. A temperature probe according to claim 1 wherein said temperature sensing elements are thermisters.

5. A temperature probe according to claim 1 wherein said needle has a range from about 5 mm to about 40 mm in length.

6. A temperature probe according to claim 1 comprising retaining means on said needle adjacent the proximal end thereof for retaining said needle in place in animal tissue.

7. A temperature probe according to claim 6 wherein said retaining means comprises an annular protuberance.

8. A temperature probe for insertion into animal tissue for determining temperature at a plurality of selected positions in the tissue, comprising:
    an elongated needle including a solid body formed of a plastic taken from the group consisting of polycarbonate, ABS, PVC, Nylon and aceytl, and having a distal end having tip means for penetrating animal tissue and a proximal end defined by an enlarged cap;
    a plurality of temperature sensing elements embedded within said needle body, said plurality of temperature sensing elements being disposed in longitudinally spaced relationship between said needle distal end and said proximal end with said sensing elements thermally isolated from each other by said plastic, one of said plurality of temperature sensing elements being positioned adjacent said tip and another of said plurality of temperature sensing elements being positioned adjacent said cap; and
    a plurality of conductive leads each connected respectively to one of said sensing elements disposed within said needle body and exiting said needle body at the proximal end thereof for connection to associated indicating means.

9. A temperature probe according to claim 8 wherein said sensing elements are thermocouples.

10. A temperature probe according to claim 8 wherein said temperature sensing elements are thermisters.

11. A temperature probe according to claim 8 wherein said needle has a length of from about 5 mm to about 40 mm.

12. A temperature probe according to claim 8 comprising retaining means on said needle adjacent the proximal end thereof, said retaining means comprising an annular generally frusto-conical protuberance.

13. A temperature probe according to claim 12 wherein said tip has a generally wedge configuration.

14. A temperature probe for insertion into animal tissue, comprising:
  an elongated needle including a solid body formed of a plastic taken from the group consisting of polycarbonate, ABS, PVC, Nylon and aceytl, and having a distal end having wedge shaped tip means for penetrating animal tissue and a proximal end defined by an enlarged cap;
  a plurality of temperature sensing elements embedded within said needle body, said plurality of temperature sensing elements being disposed in longitudinally spaced relationship between said needle distal end and said proximal end with said sensing elements thermally isolated from each other by said plastic, one of said plurality of temperature sensing elements being positioned adjacent said tip and another of said plurality of temperature sensing elements being positioned adjacent said cap;
  an annular generally frusto-conical protuberance means on said needle adjacent said cap for retaining said needle in position when inserted in tissue; and
  a plurality of conductive leads each connected respectively to one of said sensing elements disposed within said needle body and exiting said needle body at the proximal end thereof for connection to associated indicating means.

* * * * *